(12) United States Patent
Cerwin et al.

(10) Patent No.: US 6,481,568 B1
(45) Date of Patent: Nov. 19, 2002

(54) LABYRINTH PACKAGE FOR SUTURES

(75) Inventors: Robert J. Cerwin, Pipersville, PA (US); Michael Pohle, Flemington, NJ (US); Robert A. Daniele, Flemington, NJ (US); Anthony Esteves, Somerville, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/477,245

(22) Filed: Jan. 4, 2000

Related U.S. Application Data

(62) Division of application No. 09/280,106, filed on Mar. 29, 1999.

(51) Int. Cl.[7] .................................................. A61B 17/06
(52) U.S. Cl. ........................................ 206/63; 206/339
(58) Field of Search ............................... 206/63.3, 227, 206/339, 380, 382

(56) References Cited

U.S. PATENT DOCUMENTS

| | | | |
|---|---|---|---|
| 3,338,401 A | 8/1967 | Regan, Jr. ................. 206/63.3 |
| 3,972,418 A | 8/1976 | Schuler et al. ................... 17/2 |
| 4,424,898 A | 1/1984 | Thyen et al. ..................... 17/6 |
| 4,961,498 A | 10/1990 | Kalinski et al. ................. 17/6 |
| 4,967,902 A | 11/1990 | Sobel et al. ..................... 17/6 |
| 5,154,283 A | 10/1992 | Brown ............................. 17/6 |
| 5,222,978 A | 6/1993 | Kaplan et al. .................... 17/6 |
| 5,359,831 A | * 11/1994 | Brown et al. |
| 5,468,252 A | 11/1995 | Kaplan et al. .................... 17/6 |
| 5,628,395 A | * 5/1997 | Daniele et al. |
| 5,704,469 A | * 1/1998 | Daniele et al. |
| 6,076,659 A | * 6/2000 | Baumgartner et al. |

\* cited by examiner

Primary Examiner—David T. Fidei
(74) Attorney, Agent, or Firm—Emil Richard Skula

(57) ABSTRACT

A labyrinth package for sutures. The package has a base member with a top and a bottom. A labyrinth wall member extends from the top of the base member upwardly to form a labyrinth channel. The channel has an open end and a closed end. There is a vacuum opening in the bottom of the channel adjacent to the closed end. A lid is placed on top of the package. The package is loaded with sutures by using a combination of a vacuum source applied to the vacuum opening and a venturi air stream feed.

8 Claims, 6 Drawing Sheets

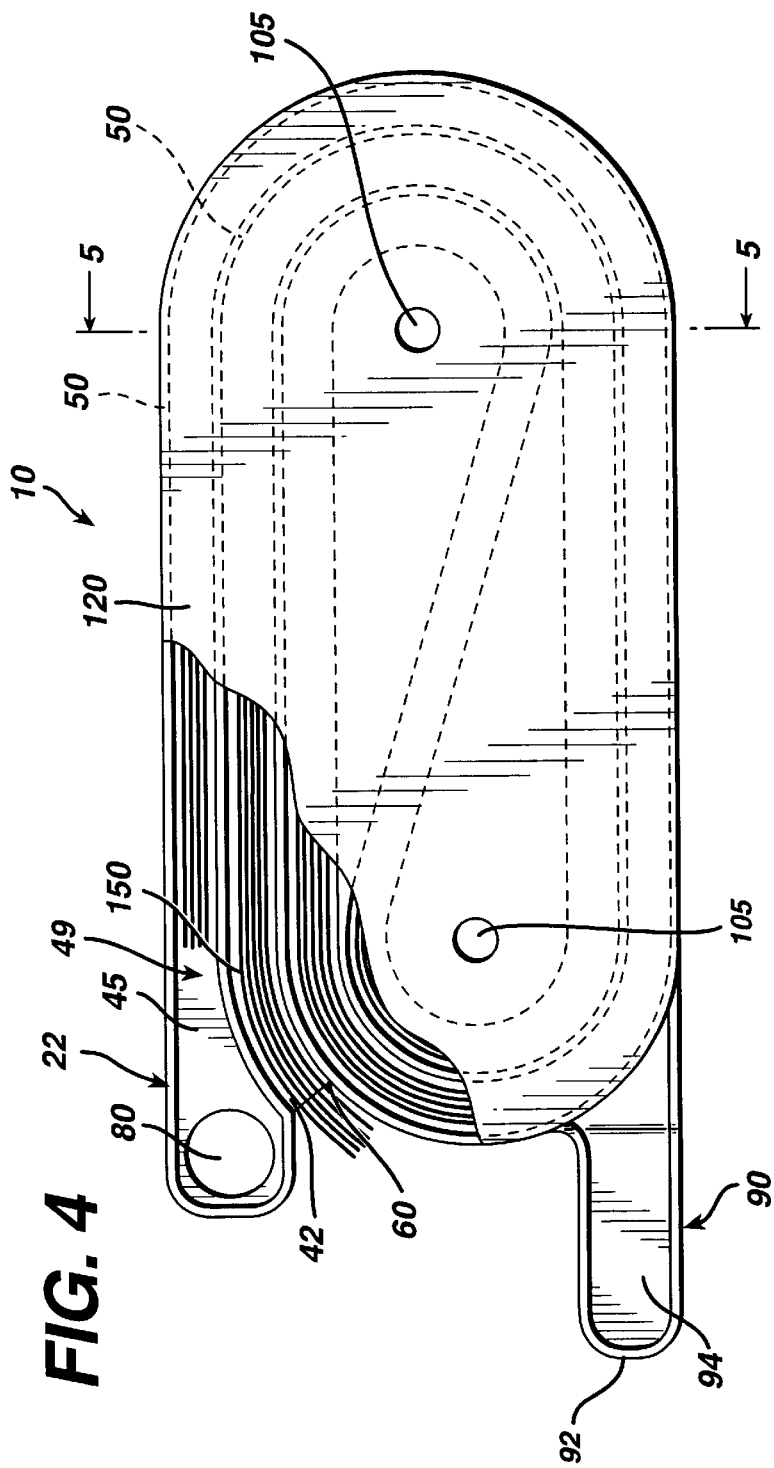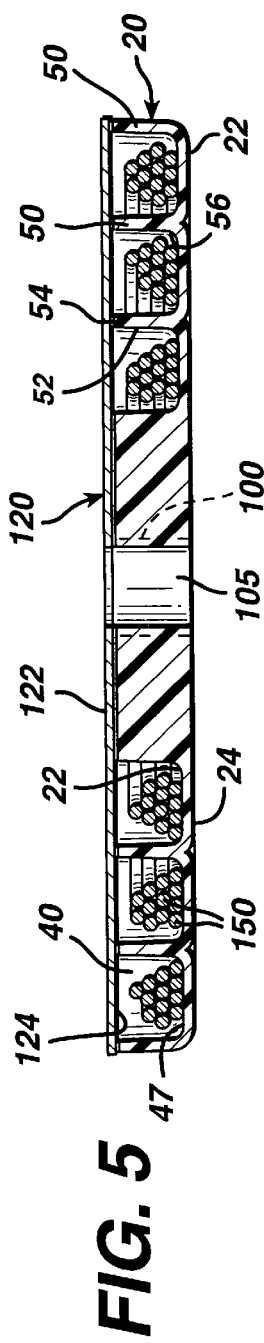

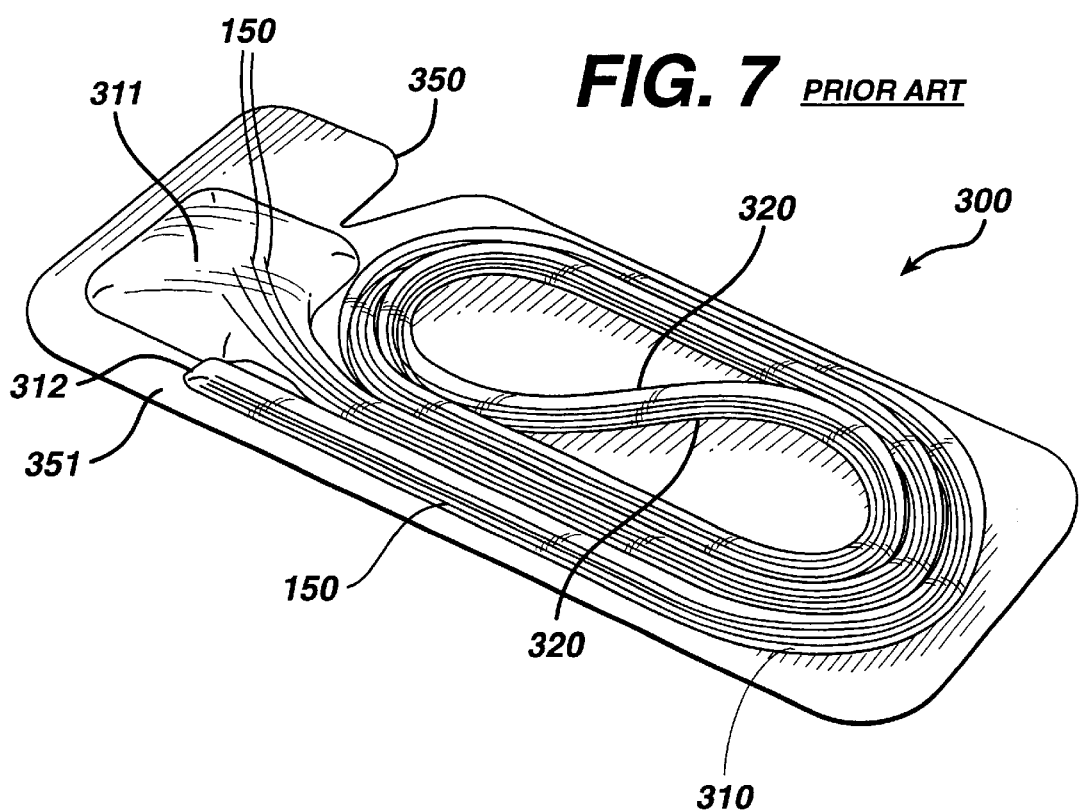

LABYRINTH PACKAGE FOR SUTURES

This application is a Div. of Ser. No. 09/280,106 filed Mar. 29, 1999.

TECHNICAL FIELD

The field of art to which this invention pertains is packaging, more specifically, packages for surgical sutures.

BACKGROUND OF THE INVENTION

Packages for surgical sutures are well known in this art. Sutures may be loaded into tray packages having a suture channel. An example of such a package is contained in U.S. Pat. No. 4,967,902, which is incorporated by reference. Trays with winding channels are also disclosed in commonly assigned, co-pending U.S. patent application Ser. No. 09/143,818 filed on Aug. 31, 1998, now U.S. Pat. No. 6,047,815 which is incorporated by reference. It is also known to package sutures in folder-panel packages. Yet another type of suture package which is known in this are is a labyrinth-type package. Examples of labyrinth packages for sutures and methods of loading such packages are contained in U.S. Pat. Nos. 3,338,401 and 3,490,192, which are incorporated by reference.

Although the packages of the prior art function adequately to contain and maintain sutures, there are disadvantages associated with their use as well. Folder-panel packages typically may impart undesirable memory to the suture, and may not dispense suture reliably. In addition, in folder packages the force to dispense suture is typically higher, and access to the suture when dispensing is less than optimal. Conventional tray packages may also impart undesirable levels of memory to the suture, depending upon the type of suture packaged therein, and may have less than optimal force to dispense and reliability of dispensing. In addition, tray packages may not always provide the best access to the sutures when dispensing. Conventional labyrinth packages may have problems associated with reliability of dispensing, and may also have size limitations. In addition, it is known that existing loading processes for labyrinth packages are burdensome and inefficient.

Accordingly, what is needed in this art are novel packages for surgical sutures, which overcome these deficiencies, along with novel loading processes for such packages.

SUMMARY OF THE INVENTION

Therefore, a novel package for surgical sutures is disclosed. The package has a base member. The base member has a top and a bottom, first and second opposed ends and a pair of opposed sides. A plurality of walls extend up from the top of the base member. The walls have tops and bottoms. The walls also have opposed sides. A labyrinth channel is formed by the walls. The channel has a bottom, opposed sides and an open top. The channel has a first open end and a second closed end. A vacuum opening extends through the bottom of the channel in the second end. There is a suture loading opening in communication with the first end. A cover is mounted to the tops of the walls, thereby enclosing the channel such that there is only access to the channel from the suture loading opening or the vacuum opening.

Another aspect of the present invention is an embodiment of the above-described package without a cover.

Yet another aspect of the present invention is a method of loading sutures into the previously-described package of the present invention having a cover. Initially, a suture package is provided. The suture package comprises the package of the present invention. The package has a base member, wherein the base member has a top and a bottom, first and second opposed ends and a pair of opposed sides. A plurality of walls extends up from the top of the base member; the walls have tops and bottoms. The walls also have opposed sides. A labyrinth channel is formed by the walls. The channel has a bottom, opposed sides and an open top. The channel has a first open end and a second closed end. A vacuum opening extends through the bottom of the channel in the second end. A suture loading opening is in communication with the first end. A cover is mounted to the tops of the walls, thereby enclosing the channel such that there is access to the channel only from the suture loading opening or the vacuum opening. Then, a plurality of surgical sutures is moved to an entrance port of a venturi. A compressed air stream is directed into the venturi such that the sutures are entrained in the air stream. The air stream and entrained sutures are directed to the suture loading opening of the package while, simultaneously, a vacuum is pulled on the vacuum port in the second end. And, the sutures are located in the labyrinth channel such that one end of each suture is contained within the second closed end of the channel, and the other end of each suture is located adjacent to the open end of the channel.

These and other advantages of the present invention will become more apparent by the following description and accompanying drawings.

BRIEF DESCRIPTION OF THE DRAWINGS

FIG. 4 is a plan view of the package of FIG. 3, after it has had a cover mounted to the tops of the walls, with sutures in the labyrinth channel; a partial cut-away of the cover is seen, revealing a portion the channel and sutures.

FIG. 5 is a cross-sectional view of the package of FIG. 4 taken along View-Line 6—6.

FIG. 7 is a perspective view of a labyrinth package of the prior art.

DESCRIPTION OF THE PREFERRED EMBODIMENT

Figure 1:
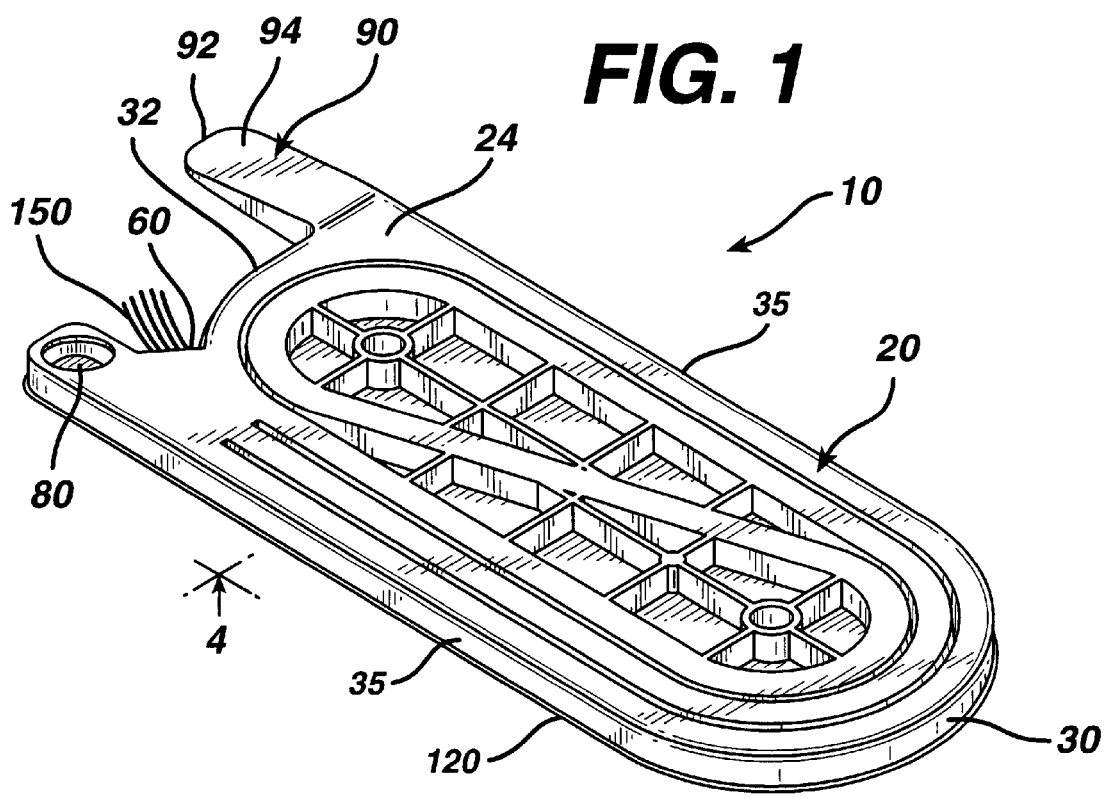
FIG. 1 is a perspective view of a package of the present invention, illustrating the bottom of the package; the package is loaded with sutures emplaced in the labyrinth suture channel, the ends of which extend out from the loading port.
Figure 2:
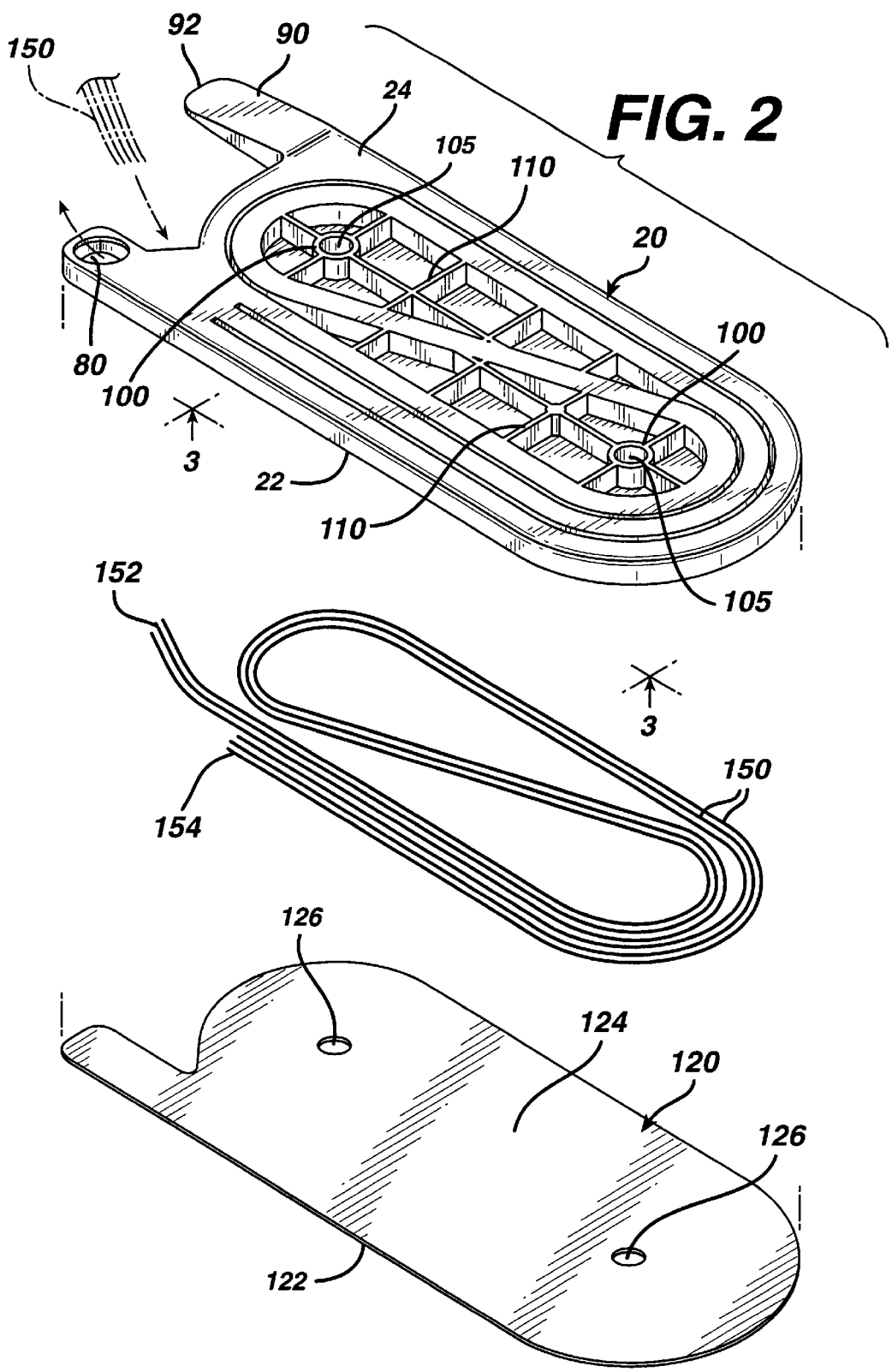
FIG. 2 is an exploded perspective view of package of FIG. 1.
Figure 3:
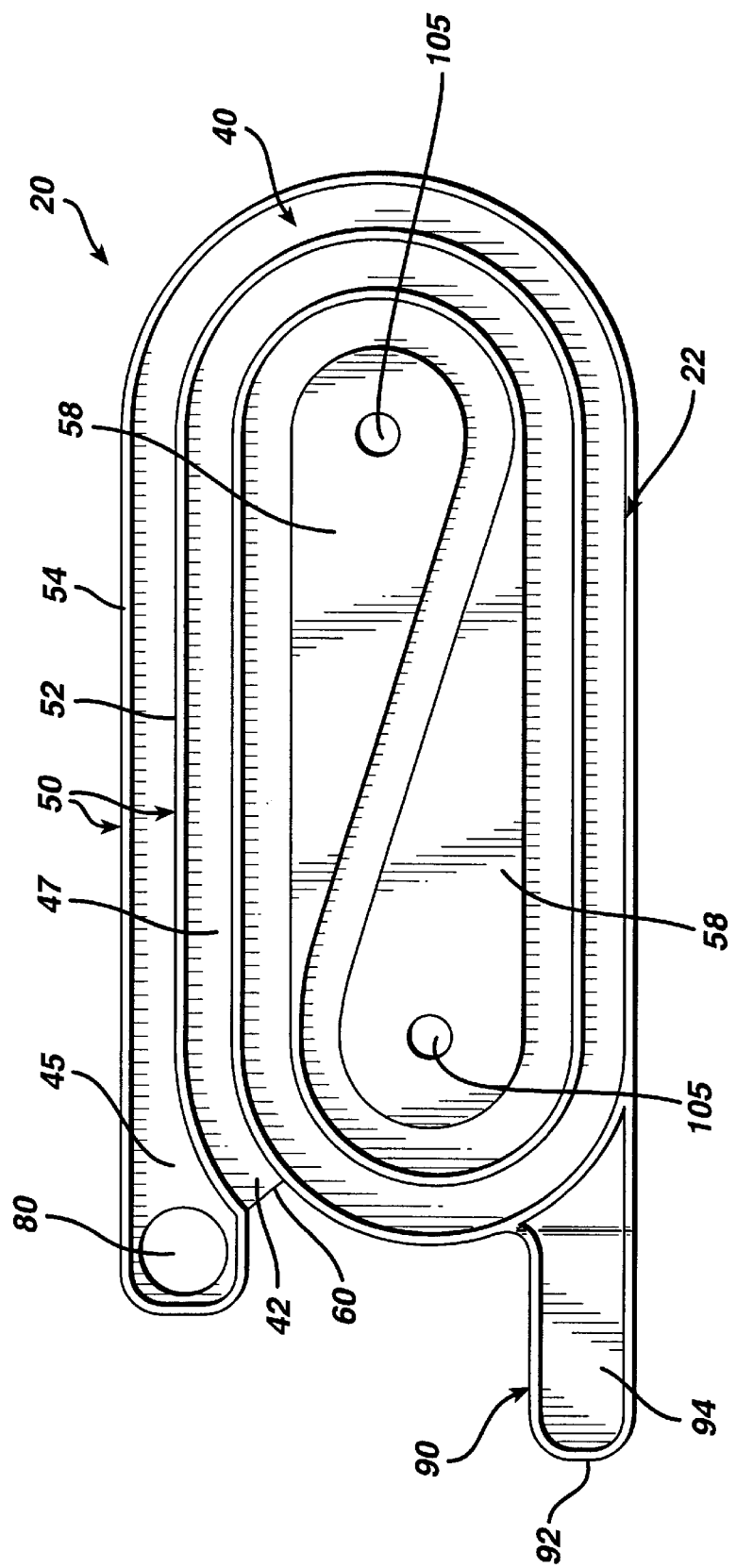
FIG. 3 is a plan view of a package of the present invention without a cover.

A package of the present invention is illustrated in FIGS. 1–5. The package 10 is seen to have base member 20 having a top 22 and a bottom 24. The package is also seen to have first semi-circular end 30 and opposed semi-circular second end 32. Connecting the first and second ends 30 and 32 are the opposed sides 35. Extending up from the top 22 of the base member 20 are the walls 50. The walls 50 are seen to have sides 52, tops 54, and bottoms 56. The tops 54 of walls 50 are seen to widen along sections 58 toward the interior of the base member 20. The walls 50 are arranged in a labyrinth-like manner to form the labyrinth channel 40. The labyrinth channel 40 is seen to have first open end 42, closed end 45, and bottom 47. Open end 42 is in communication with the suture loading and withdrawal port 60. Bottom 47 of channel 40 is the top 22 of base member 20. Channel 40 also has open top 49. The sides of the channel 40 are formed by the sides 52 of the walls 50. Extending longitudinally outward from the open end 42 is the locator extension member 90. Locator extension end 90 is a generally rectangular flat member having an outer curved end 92 and a top surface 94. Locator end 90 is preferably configured to have top surface 94 sloped downward toward end 92 to from a ramped structure. Contained in the base member 20 adjacent to closed end 45 is the vacuum opening 80 which is in communication with channel 40.

Extending up from the top 22 of the base member 20 are a pair of hub members 100 containing pin openings 105. A plurality of intersecting reinforcing ribs 110 and 120 are seen to connect the hubs 100 to the walls 50. Mounted in the tops 54 of the walls 50 is the containment lid 120. Containment lid 120 has top 122 and bottom 124. The bottom 124 is mounted on top of the tops 54 in a conventional manner for example by heat sealing, adhesives, rivets, fasteners, welding, and the like. The lid 120 is also seen to have pin openings 126 for receiving winding pins or locating pins. Suture 150 having first end 152 and second end 154 is seen to be loaded into the channel 40 such that the end 152 of the suture 150 extends out from channel port 60, while the second end 154 of the suture 150 is in end 47 and in close proximity to vacuum opening 80. The packages of the present invention may be used for single sutures or multiple sutures.

Figure 6:
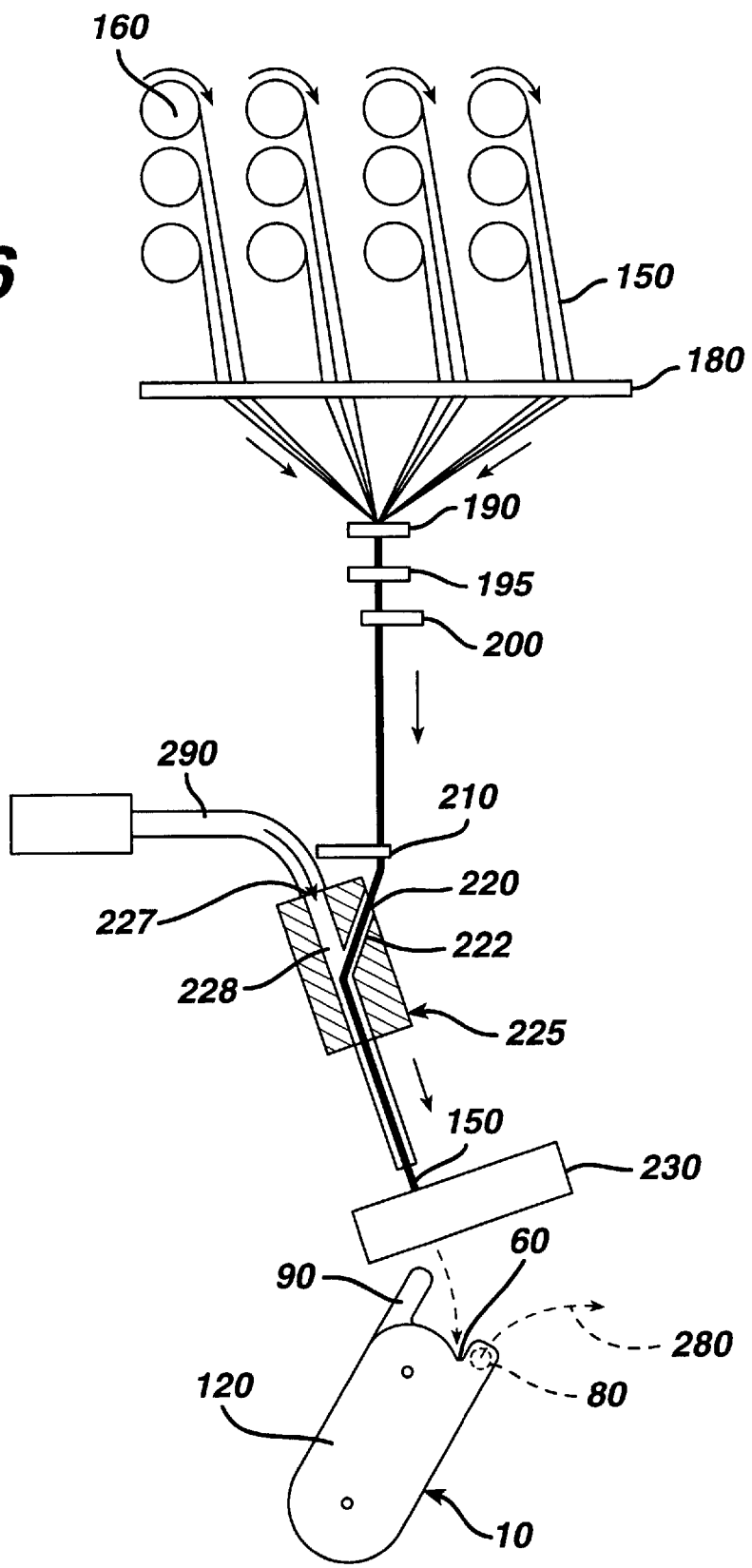
FIG. 6 is a schematic flow diagram of a loading process of the present invention for loading sutures into the packages of the present invention.

Referring now to FIG. 6, a schematic diagram of a loading process for loading multiple surgical sutures 150 into a package 10 of the present invention is illustrated. Initially, prior to loading, conventional surgical suture 150 which has been previously wound on to reel members 160, is mounted in a conventional rack allowing the reels 160 to rotate as suture 150 is withdrawn from the reels 160 through first eyelets 180. From the eyelets 180, the strands of suture 150 are fed into single eyelet 190 such that the sutures are no longer singulated. Conventional gripping clamps 195, 200 and 210 grip the sutures 150. Clamps 95 and 210 are stationary, while clamp 200 is moveable. At the start of each loading cycle, clamps 195 and 210 are opened, while clamp 200 remains closed. Clamp 200 moves and causes sutures 150 to be unwound from reels 160 as it moves the gripped sutures 150 through cutter 230 into venturi port 220 and channel 222 of venturi 225. At this point of the process, clamp 210 is open as previously mentioned. A stream of compressed air 290 is directed to the other port 227 of venturi 225 and into channel 228, which is intersected by channel 222, thereby causing a venturi effect which pulls the suture through the port 220, and through channels 222 and into and out of channel 228 as the clamp 200 moves toward the open clamp 210. A package 10 of the present invention is provided and mounted in a conventional loading fixture having mounting pins, the pins are contained within pin openings 105. At the same time a conventional source of vacuum 280 is connected to the vacuum opening 80 such that the combination of the vacuum which is pulled on port 80 and the venturi effect created by venturi 225 entrain sutures 150 in stream 290 thereby causing a predetermined length of sutures 150 to be loaded through port 60 and into the channel 40. Once the predetermined length of sutures 150 is loaded into channel 40, the cutting blade 230 cuts the sutures 150 and the loading of the package 10 is then completed. After the sutures 150 are cut by the cutting blade 230, clamps 195 and 210 once again clamp the suture 150 to prevent passage through the clamp and the clamp 200 cycles back to the starting position to once again engage suture. When the starting cycle starts again, the clamp 200 engages sutures as the clamps 195 and 210 open. The clamp 200 once again moves sutures 150 toward the clamp 210 and the venturi 225. The package 10, loaded with sutures 150, is then removed from the holding fixture and may then be packaged in a conventional outer package, such as a foil pouch or a TYVEK spun bonded polyethylene pouch, and subsequently sterilized utilizing a conventional sterilization system such as, for example, ethylene oxide gas, radiation or autoclaving.

The amount of compressed air which is fed into conventional venturi 225 is sufficient to provide a sufficient pressure drop adjacent to opening 220 to pull sutures through the venturi and to assist in moving them into the channel 40 of package 10 in aair stream 290. The air flow or air stream from the compressed air source through the venturi passage 227 will again be sufficient to provide an adequate venturi effect in passage 220 effective to assist in pulling sutures through the passage. The rate of air flow will vary in accordance with the size of the suture and the size of the venturi. The vacuum 180, which is applied to the vacuum opening 80, will be sufficient to effectively assist in pulling the sutures 150 into the passage 40 in combination with the airflow form venturi 225. The loading process of the present invention is advantageous in that it is greatly facilitated by the use of a venturi device and air stream along with vacuum source to load sutures into labyrinth packages. It has previously not been known to use such a venturi device and air stream in combination with a vacuum and it has been found that the combination greatly enhances the loadability of suture into labyrinth package.

The labyrinth packages of the present invention are distinguishable over the packages of the prior art, for example as seen in FIG. 7. FIG. 7 illustrates a package 300 of the prior art. This is a thermoformed package wherein each labyrinth channel 310 has a double wall 320 surrounding it, as opposed to the packages 10 of the present invention which have a single wall 50 separating the labyrinth pathways from each other. This prevents sutures 150 from hanging up between the tops of the walls 50 and the bottom of the top lid 120. In addition, in order to load the package 300 of the prior art, it is necessary to peel back the foil top lid 350 at section 351 prior to loading the channel 310 to expose the open ends 311 and 312 of the labyrinth channel. Vacuum is applied to the end 311 of the labyrinth channel 310 in order to suck the sutures 150 into the labyrinth channel 310. This peeled back section must then be reattached.

The packages of the present invention may be manufactured from conventional thermoplastic or thermoformable moldable materials. It is especially preferred to use polyolefin materials such as polyethylene, polypropylene and polyesters such as nylon, and equivalents thereof. Preferably the packages of the present invention may be injection molded, however, the packages may also be formed by other conventional processes.

The lids useful for the packages of the present invention can be made from conventional flexible sheet materials such as paper, spun-bonded polyethelene, polyolefins and the like. The sutures which can be packaged in the packages of the present invention include conventional absorbable and non-absorbable sutures and equivalents thereof.

The packages 10 of the present invention have many advantages over the packages of the prior art. First of all, it is easier to load the packages of the present invention having a vacuum opening in the bottom of the labyrinth channel 40. In addition, the packages of the present invention utilize a single wall construction between the channels, thereby providing the advantage of preventing suture from locking up by being wedged between the top of the walls 50 and the bottom of the lid 120. The packages of the present invention also allow for using sharper radiused labyrinth passageways without adversely affecting the reliability of withdrawing sutures from the passageway, and also without adversely imparting an undesirable memory to the sutures.

Although this invention has been shown and described with respect to detailed embodiments thereof, it will be understood by those skilled in the art the various changes in form and detail thereof may be made without departing from the spirit and scope of the claimed invention.

We claim:

1. A package for surgical sutures, comprising:
   a base member, said base member having a top and a bottom, first and second opposed ends and a pair of opposed sides;
   a plurality of walls extending up from the top of the base member, the walls having tops and bottoms, said walls having sides;
   a labyrinth channel formed by said walls, said channel having a bottom, opposed sides and an open top, said channel having a first open end and a second closed end;
   a vacuum opening extending through the bottom of the channel in the second end;
   a suture loading opening in communication with the first end;
   a locating extension member extending longitudinally outward from the base member; and,
   a cover mounted to the tops of the walls, thereby enclosing the channels such that there is only access to the channel from the suture loading opening or the vacuum opening.

2. The package of claim 1 further comprising a member projecting from one end of the base member adjacent to the loading port.

3. The package of claim 1 additionally comprising a pair of pin retention holes extending through the base member.

4. The package of claim 1 additionally comprising a suture loading port in communication with the first open end of the channel.

5. A package for surgical sutures, comprising:
   a base member, said base member having a top and a bottom, first and second opposed ends and a pair of opposed sides;
   a plurality of walls extending up from the top of the base member, the walls having tops and bottoms, said walls having sides;
   a labyrinth channel formed by said walls, said channel having a bottom, opposed sides and an open top, said channel having a first open end and a second closed end;
   a vacuum opening extending through the bottom of the channel in the second end;
   a locating extension member extending longitudinally outward from the base member; and,
   a suture loading opening in communication with the first end.

6. The package of claim 5 further comprising a member projecting from one end of the base member adjacent to the loading port.

7. The package of claim 5 additionally comprising a pair of pin retention holes extending through the base member.

8. The package of claim 5 additionally comprising a suture loading port in communication with the first open end of the channel.

\* \* \* \* \*